(12) United States Patent
Li et al.

(10) Patent No.: US 8,206,935 B2
(45) Date of Patent: Jun. 26, 2012

(54) METHOD OF RAPIDLY QUANTIFYING HYDROXYMETHYLATED DNA

(76) Inventors: Weiwei Li, Lindenhurst, NY (US); Jessica Li, Lindenhurst, NY (US)

( * ) Notice: Subject to any disclaimer, the term of this patent is extended or adjusted under 35 U.S.C. 154(b) by 208 days.

(21) Appl. No.: 12/803,666

(22) Filed: Jul. 1, 2010

(65) Prior Publication Data

US 2012/0003663 A1    Jan. 5, 2012

(51) Int. Cl.
*G01N 33/53* (2006.01)
(52) U.S. Cl. ............................................. 435/7.1; 435/4
(58) Field of Classification Search ........................ None
See application file for complete search history.

(56) References Cited

U.S. PATENT DOCUMENTS 6,127,115 A * 10/2000 Ragland et al. .............. 435/6.12
7,785,793 B2 * 8/2010 Li et al. ........................ 435/6.18

OTHER PUBLICATIONS

Inouye et al. (J. Clinical Microbiology 1990 vol. 28, p. 1469-1472).*

* cited by examiner

*Primary Examiner* — Jacob Cheu (57) ABSTRACT

This invention is related to a method for rapidly quantifying hydroxymethylated DNA by binding DNA to a plastic carrier followed by immunodetection of 5-hydroxymethylcytosine or a hydroxymethylcytosine structure that is marker of DNA hydroxymethylation.

12 Claims, 5 Drawing Sheets

METHOD OF RAPIDLY QUANTIFYING HYDROXYMETHYLATED DNA

CROSS-REFERENCE TO RELATED APPLICATIONS

Not applicable

STATEMENT REGARDING FEDERALLY SPONSORED RESEARCH OR DEVELOPMENT

Not applicable

REFERENCE TO A MICROFICHE APPENDIX

Not applicable

BACKGROUND OF THE INVENTION

1. Field of the Invention

This invention is related to a method for rapidly quantifying hydroxymethylated DNA by binding DNA to plastic carrier followed by immunodetection of 5-hydroxymethylcytosine or hydroxymethylcytosine structure that is a marker of DNA hydroxymethylation.

2. Description of the Related Art

DNA methylation is an epigenetic modification which is catalyzed by DNA cytosine-5-methyltransferases (DNMTs) and occurs at the 5-position (C5) of the cytosine ring, within CpG dinucleotides. DNA methylation is essential in regulating gene expression in nearly all biological processes including development, growth, and differentiation (Laird P W et al: Annu Rew. Genet, 1996; Reik W et al: Science, 2001; Robertson K D et al: Nature Rew. Genet, 2005). Alterations in DNA methylation have been demonstrated to cause change in gene expression. For example, hypermethylation leads to gene silencing or decreased gene expression while hypomethylation activates the genes or increases gene expression. Region-specific DNA methylation is mainly found in 5'-CpG-3' dinucleotides within the promoters or in the first exon of genes, which is an important pathway for the repression of gene transcription in diseased cells.

Very recently, a novel modified nucleotide, 5-hydroxymethylcytosine (5-hmC) has been detected to be abundant in mouse brains and embryonic stem cells (Kriaucionis S et al: Science, 2009). 5-Hydroxymethylcytosine was first seen in bacteriophages in 1952 (Wyatt G R et al: Nature, 1952). In mammals, it can be generated by oxidation of 5-methylcytosine, a reaction mediated by the Tet family of enzymes and Dnmt proteins (Tahiliani M et al: Science, 2009). 5-hmC is a hydroxylated and methylated form of cytosine. The 5-hydroxymethylcytosine structure may include 5-methylhydroxycytidine, and 5-hydroxymethyl-2-deoxy-cytidine, and further include 5-hydroxymethyl-2-deoxy-cytidine monophosphate (hmdCMP), 5-hydroxymethyl-2-deoxy-cytidine diphosphate (hmdCDP), and 5-hydroxymethyl-2-deoxy-cytidine triphosphate (hmdCTP). The broader function of 5-hmC in epigenetics is still a mystery today. However, a line of evidence showed that 5-hmC plays a role in DNA demethylation, chromatin remodeling and gene expression regulation, specifically in brain-specific gene regulation (Valinluck V et al: Cancer Res, 2007, Valinluck V et al: Nucleic Acid res, 2004, Penn N W et al: Biochem J, 1976, Penn N W et al: biochem J, 1972):

1) Conversion of 5-methylcytosine (5-mC) to 5-hmC greatly reduced affinity of MBD proteins to methylated DNA;

2) The observation that formation of 5-hmC by oxidative damage or by the addition of aldehydes via Dnmts prevents Dnmt-mediated methylation of target cytosine.

3) 5-hmC may recruit specific binding proteins that alter chromatin structure or DNA methylation patterns.

4) 5-hmC accounts for roughly 40 percent of the methylated cytosine in Purkinje cells and 10 percent in granule neurons.

Because of the presence of 5-hmC in DNA with an unclear function in gene regulation and the discovery of the enzymes that produce 5-hmC, it is considered important to know the distribution of this base in different cell types and in different compartments of the genome of mammalians. It is particularly important to identify hydroxymethylation status in human cell/tissues with and without diseases. Currently used methylated DNA analysis methods including restriction enzyme digestion, bisulfite or MeDIP-mediated MS-PCR and sequencing have been demonstrated to not be suitable for 5-hmC or hydroxymethylated DNA detection as 5-hmC and 5-mC are virtually indistinguishable with these methods (Huang Y et al: PLoS One, 2010; Jin S G et al: Nucleic Acid Res, 2010, Nestor C et al: BioTechniques, 2010). Several chromatography-based techniques such as HPLC and TLC mass spectrometry are used for detecting 5-hmC (Kriaucionis S et al: Science, 2009; Penn N W et al: biochem J, 1972). In the analysis, DNA is digested into single nucleotides and total genomic 5-hmC is quantified. However these methods are labor intensive, time-consuming, or require large amounts of DNA (>250 ng) as the starting material for measurement, or rely on the use of expensive equipment. These disadvantages lead to cost-ineffectiveness, low throughput and inconvenience for routine application in most health and medical institutions. Thus, there is a need to establish a method to improve the detection of 5-hmC or hydroxymethylated DNA.

BRIEF SUMMARY OF THE INVENTION

The present invention provides a simple method that can rapidly quantify hydroxymethylated DNA through the immunodetection of 5-hmC structure comprising the step of:

1) Isolation and purification of DNA from biological materials;
2) Binding of DNA to a plastic carrier with a DNA high-binding solution which consists of several salts mixed in an appropriate ratio;
3) 
4) Detection of 5-hmC structure contained in the DNA with an anti-5-hmC specific antibody;
5) Detection of anti-5-hmC antibody with a secondary antibody conjugated with label molecules;
6) Fluorescent or color development of antibody conjugated with label molecules and the quantification of fluorescent or color intensity.
7) Use hydroxymethylated DNA containing a known amount of 5-hmC standard control for calculating hydroxymethylated DNA amount of DNA samples.

Thus the invention allows for a rapid quantification of hydroxymethylated DNA to be achieved. The invention is based on the finding that multiple salt-based solution can more rapidly and conveniently enhance DNA binding and retention on a plastic surface at an appropriate temperature. The invention is also based on the finding that the immunodetection of 5-hmC can be quantitatively achieved through specific antibody recognition followed by color or fluorescence development and measurement. Therefore the method presented in this invention significantly overcomes the weaknesses existing in the prior technologies and enables hydroxymethylated DNA to be quantified rapidly and efficiently.

DETAILED DESCRIPTION OF THE INVENTION

Figure 1:
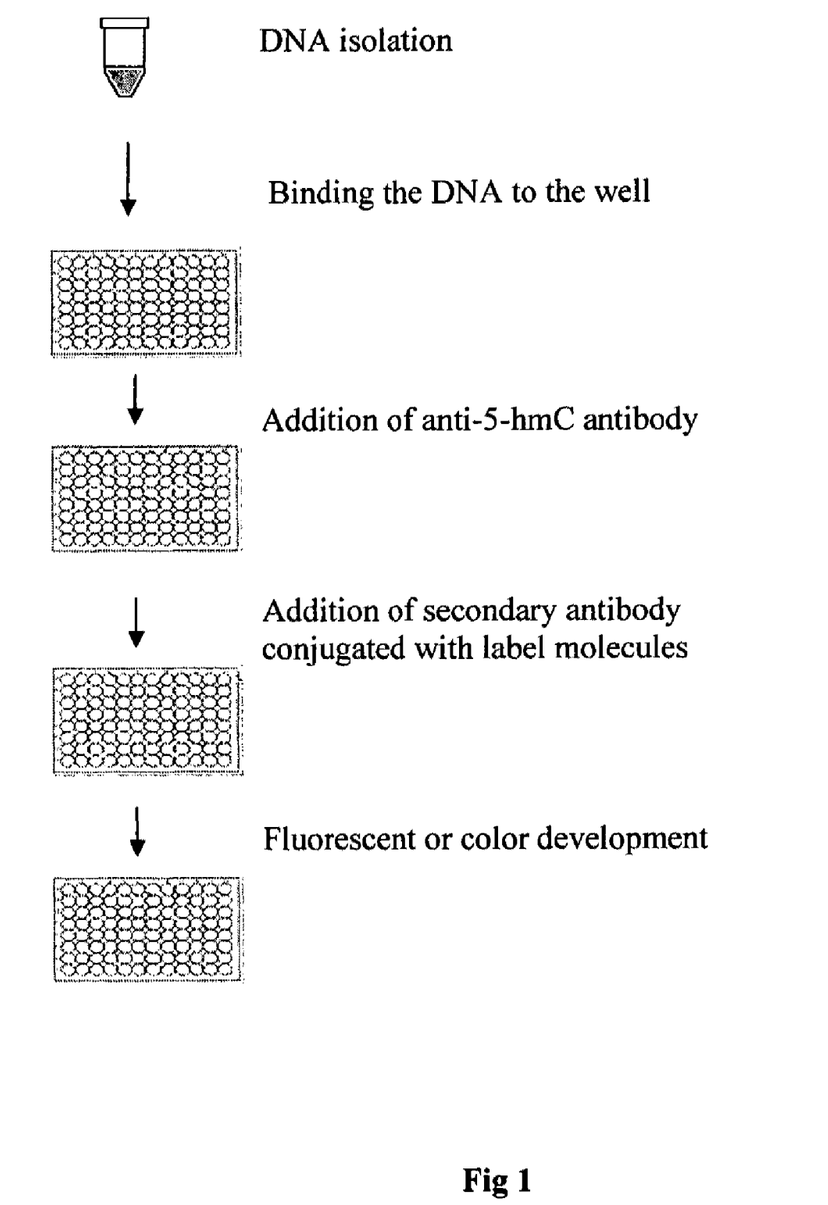
FIG. 1 shows a diagram of the rapid process for quantifying hydroxymethylated DNA. The process involves: (1) binding of DNA on the plastic well with DNA high-binding solution; (2) detection of 5-hydroxymethylcytosine structure contained in the DNA with the anti-5-hmC specific antibody; (3) detection of anti-5-hmC antibody with a secondary antibody conjugated with label molecules; and (4) fluorescent or color development of antibody conjugated label molecules and quantification of fluorescent or color intensity.

The present invention provides a method for rapidly quantifying hydroxymethylated DNA by binding DNA on the plastic carrier followed by immunodetection of 5-hydroxymethylcytosine structure that is a marker of DNA hydroxymethylation. A basic outline of the method presented in this invention is described in FIG. 1. This method is particularly useful for rapidly completing a hydroxymethylated DNA assay in a short time. This method is also particularly useful for quantifying hydroxymethylated DNA in a high throughput format.

According to the method of this invention, DNA could be isolated by lysis of cells with a lysis buffer containing a sodium salt, tris-HCl, EDTA, and detergents such as sodium dodecyl sulphate (SDS) or cetyltrimethylammonium bromide (CATB). Tissue fragments should be homogenized before lysing. For example, disaggregating of tissue fragments can be performed by stroking 10-50 times, depending on tissue type, with a Dounce homogenizer. DNA can be further purified by mixing with a high concentration of sodium chloride and then adding into a column pre-inserted with a silica gel, a silica membrane, or a silica filter. The DNA that binds to the silica matrix is washed by adding a washing buffer and eluted with TE buffer or water. DNA can also be isolated and purified by using commercially available DNA extraction kits such as QiaAmp blood or tissue kits. The starting materials for DNA extraction can be from various forms including, but not limited to, fresh tissues, frozen tissues, formalin fixed and paraffin embedded tissues, body fluids, and cultured cells.

The purified DNA can be then bound to the plastic carrier by using the DNA high-binding solution containing multiple salts mixed with an appropriate ratio. The carrier should have highly hydrophobic surface properties and include but are not limited to polystyrene plastic, glass, silica coated with hydrophobic group on the surface. The carrier could be in various sizes and forms including, but not limit to beads in size of 10 nm to 100 µm, strips with 8-wells to 12-wells, microplate with 6 wells to 1516 wells, microscopic slide with or without wells, and microarray slides with or without wells. Preferably, the plastic microplate or strips are more suitable to be used in the method of this invention, as these carriers are easily handled in a rapid and high throughput format. The DNA high-binding solution contains at least one salt selected from sodium chloride, sodium sulfate, ammonium chloride, and ammonium sulfate at a concentration of 0.5 to 3 M. Preferably, the DNA high-binding solution contains multiple salts consisting of sodium chloride, ammonium chloride, and ammonium sulfate. For the DNA high-binding solution containing multiple salts, each salt solution is prepared separately at an appropriate concentration and then mixed in an appropriate ratio to yield the optimized efficiency for DNA covalent attachment to the carrier. The final concentration of various salts in the DNA high-binding solution is 0.3 to 3 M for sodium chloride and ammonium sulfate, and 0.06 to 0.6 M for ammonium chloride, respectively. The mole ratio of sodium chloride:ammonium sulfate:ammonium chloride is 5:5:1. For 96-well microplates or 8-well strips, 100 ul of the DNA high-binding solution are added followed by adding 2-10 ul of DNA. The microplate or strip is incubated at 37° C. with or without humidity for 90 min. For beads, DNA is first mixed with the DNA high-binding solution and 200 ul of the mixed DNA solution is added to the beads. The beads are incubated at 37° C. with or without humidity for 90 min. For microscopic or microarray slides, DNA is first mixed with DNA high-binding solution and 0.2 to 4 ul of the mixed DNA solution, depending on the required number of spots, is added to each spot area. The slide can be incubated at 37° C. without humidity for 45 min to dry the spotted area. DNA amount to be immobilized can be from 10 to 200 ng, preferably, from 50 to 200 ng, and more preferably, 200 ng. A 200 ng of DNA amount would ensure the tiny amount of hydroxymethylated fraction contained in DNA to be detectable while still allowing high specificity to be achieved.

According to the method of the invention, the antibody specific to the 5-hmC is added and reacted with the 5-hmC contained in DNA immobilized on the carrier. The plastic carrier is then washed with the washing buffer comprising tris-saline and 0.05% tween-20, preferably comprising phosphate saline and 0.1% tween-20. Once the washing is completed, the 5-hmC antibody is added to the plastic carrier. The antibody specific to the 5-hmC may include mouse monoclonal IgG, rat monoclonal IgG, rabbit polyclonal IgG, goat polyclonal IgG and sheep polyclonal IgG. The antibody can be unconjugated or conjugated with biotin, or enzymatic label molecules such as HRP and AP, or fluorescent label molecules such as cy3, cy5, FITC, or gold label molecules, or quantum dot label molecules. The final concentration of the antibody added to the plastic carrier should be 0.5-1 µg/ml. The plastic carrier is incubated at room temperature for 1 h at 37° C. for 45 min after adding the antibody. After incubation, the plastic is washed with wash phosphate-saline containing 0.1% tween-20 for 3 times. If the conjugated antibody is used, a colorimetric or fluorescent development can be directly carried out followed by signal measurement. If the unconjugated antibody is used, a secondary anti-mouse, or anti-rabbit, or anti-goat or anti-sheep antibody conjugated with label molecules is added to the plastic carrier. The final concentration of the secondary antibody can be from 0.01 µg/ml to 0.5 ug/ml. The label molecules, depending on the requirement of the assay, include but are not limited to horse radish peroxidase (HRP), alkaline phosphotase (AP), biotin, fluorescein (FITC), Cy3, Cy5, rhodamine, dynabeads, texas red, Alexa fluor, BODIPY, captivate ferrofluid, cascade blue, beta-lactamase, marine blue, nanogold, Oregon green, pacific blue, and quantum dot. After washing with phosphate-saline buffer containing 0.1% Tween-20, the methylated DNA can be quantitatively detected through colorimetric or fluorescent development. For colorimetric development, the solution containing color-forming substrates is added to react with enzymatic label molecules such as HRP or AP to yield blue solution or deposit. Other suitable color-forming substrates will be apparent to persons skilled in the art. For fluorescent measurement, fluorescent intensity is directly ditected with a fluorescent spectrophotometer, fluorescent scanner, or fluorescent microscope.

According to the invention, 5-hmC polyclonal antibody can be commercially available or generated by using an Abgent protocol: (1) Preparation of 5-hydroxymethylcytidine—KLH conjugates. KLH may be modified with 3-sulfo-N-hydroxysuccinimide ester sodium salt before conjugation. The conjugates of KLH-5-hmC can be identified by ultraviolet spectrophotometry. (2) Injection of KLH-5hMC into rabbits. Injections of the antigen are given in multiple sites to stimulate the best immunity. The rabbits are boosted at 21 day intervals until peak antibody titers are reached (6-8 re-immunizations); (3) Blood sample collection. Blood is collected from the central ear artery and allowed to clot and retract at 37° C. overnight. The clotted blood is then refrigerated for 24 hours before the serum is decanted and clarified by centrifugation; (4) ELISA test of antibody titers and affinity purification DNA hydroxymethylated at every 5-cytosine (5-C) can be used as the positive control. To prepare the positive control, PCR amplicons with a length of 357 bp were generated using human MLH1 promoter derived sequences by incorporating dhmCTP (5-hydroxy-methylcytidine) with dATP, dGTP, and dTTP. DNA methylated at every 5-cytosine is used as the comparative control. To prepare the comparative control, PCR amplicons with a length of 357 bp were generated using human MLH1 promoter derived sequences by incorporating dmCTP (5-methylcytidine) with dATP, dGTP, and dTTP. DNA unmethylated at every 5-cytosine is used as the negative control. To prepare the negative control, PCR amplicons with a length of 357 bp were generated using human MLH1 promoter derived sequences by incorporating dCTP (5-cytidine) with dATP, dGTP, and dTTP. The positive control, comparative control, and negative control contain 25% of 5-hmC, 5-mC and 5-C, respectively.

According to the invention, all of the components for DNA isolation, purification, plastic carrier, substances for DNA high-binding, and detection antibodies are commercially available. This invention also provides a kit containing all components required for the rapid quantification of hydroxymethylated DNA in a multi-well microplate/strip format. The kit includes: (a) a rabbit polyclonal antibody specific for 5-hydroxymethylcytosine structure and an anti-rabbit antibody conjugated with HRP; (b) a microwell strip or microwell plate; (c) the DNA high-binding solution; (3) the concentrated washing buffer comprised of phosphate-saline and surfactants; (d) a colorimetric development solution containing a color-forming substrate specific for HRP; (e) a positive control and a negative control; and (h) an instruction for conducting an assay according to the method of this invention. In one embodiment, the kit further comprises of selected components to meet the requirements for using different measurement equipment.

It is unexpected that the DNA high-binding solution consisting of multiple salts mixed in an appropriate ratio dramatically increases the binding of DNA to a plastic carrier having a highly hydrophobic surface. It is also unexpected that the DNA high-binding solution enables non-specific background binding resulting from antibodies or labeling moieties to be extremely low so that the block step with block buffer can be eliminated. Further, it has been discovered that the use of the method of this invention is able to drastically reduce the cost and time required for quantifying hydroxymethylated DNA. It has also been discovered that the use of the method of this invention is able to allow hydroxymethylated DNA quantification to be much easier and more convenient than currently used methods, as the method based on this invention can be carried out with common equipment such as a microplate reader or microscope. It has been further discovered that the use of the method of this invention enables the quantification of hydroxymethylated DNA to be performed in a high throughput format with high sensitivity and specificity, and to be completed with excellent reproducibility. The detection limitation of the method of this invention is as low as 10 pg of 5-hmC and discrimination ratio of both 5-hmC:5-mC and 5-hmC:5-C is up to 1:10000.

The method of this invention for quantifying global DNA methylation is further illustrated in the following examples:

EXAMPLE 1

The experiment was carried out to compare the effect of different DNA high-binding solution on the detection of hydroxymethylated DNA.

Figure 2:
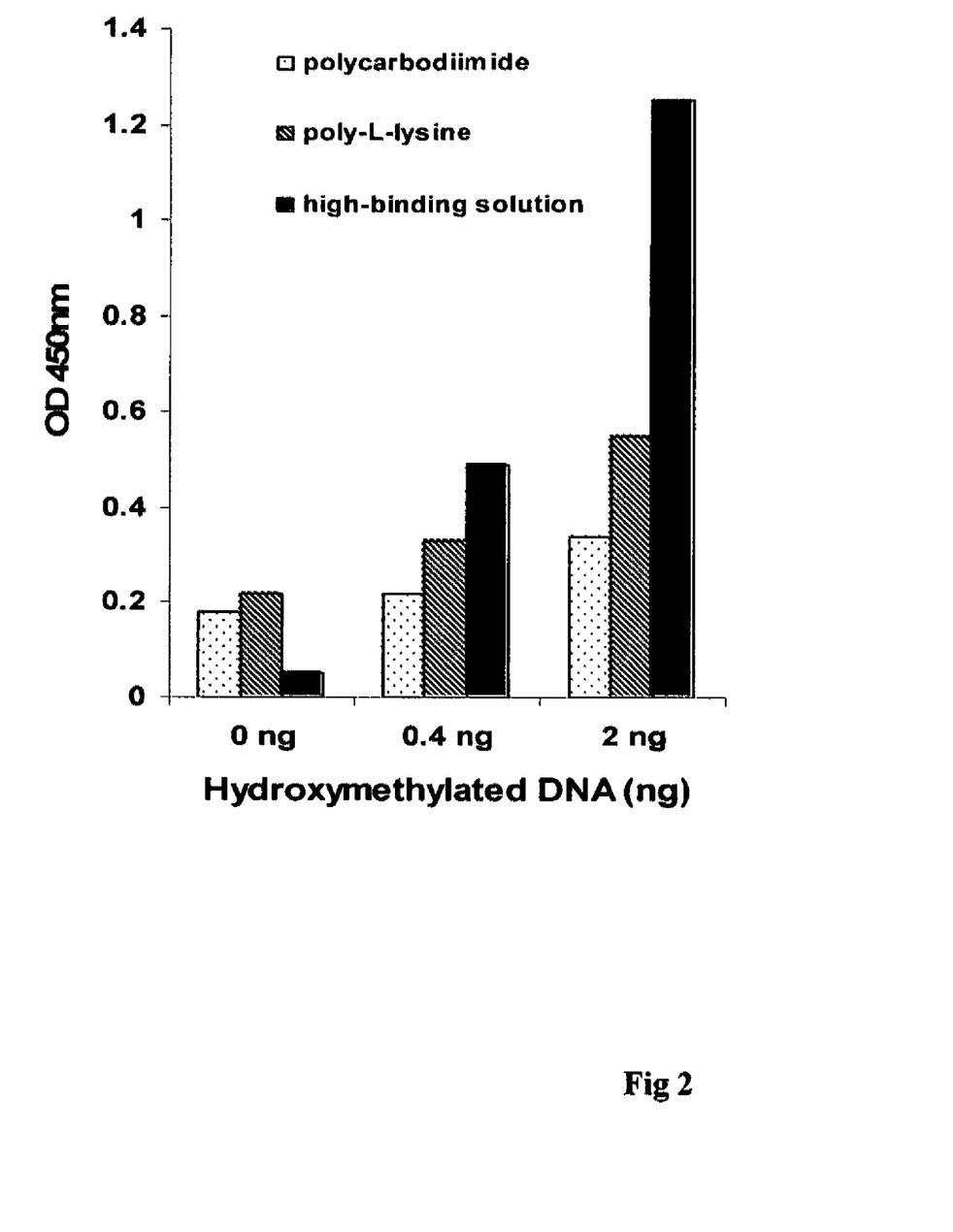
FIG. 2 shows the DNA high-binding solution containing multiple salts mixed with an appropriate ratio efficiently increases detection of hydroxymethylated DNA. The experiment was carried out as described in Example 1

In group 1, polystyrene 8-well strips were coated with 0.01% poly-L-lysine, or 1% polycarbodiimide. After storage at 4° C. for 2 weeks, the coated and uncoated strips were used for DNA high-binding. 30 µl of hydroxymethylated MLH1 amplicon at different concentrations were added into the strip wells. The strips were then incubated at 37° C. for 1.5 h followed by incubation at 60° C. for 30 min to dry the wells. The wells were blocked with 2% BSA solution at 37° C. for 30 min followed by washing 3 times. 50 µl of polyclonal anti-5-hmC antibody was then added at 0.5 µg/ml and incubated at room temperature for 1 h. The wells were washed 3 times with PBS containing 0.1% tween-20 after the antibody solution was removed. 50 µl of anti-rabbit antibody conjugated with biotin at 0.1 µg/ml was added into the wells and incubated at room temperature for 30 min. The wells were washed 4 times with PBS containing 0.1% tween-20 after the antibody solution was removed. 50 ul of streptivadin conjugated with HRP was added into the wells and incubated at room temperature for 30 min. After washing 4 times, 100 µl of the color development solution containing TMB was added into the wells and the wells were observed for 2-10 min for a blue color appearance. The 1 M HCl or $H_2SO4$ solution was added to stop the color development and the optical density was measured with a microplate reader. In group 2, 100 µl of the DNA high-binding solution based on this invention are added into polystyrene 8-well strips followed by adding 5 µl of DNA samples at different concentrations. The strips were then incubated at 37° C. for 1.5 h followed by washing 3 times. 50 µl of polyclonal anti-5-hmC antibody was then added at 0.5 µg/ml and incubated at room temperature for 1 h. The wells were washed 3 times with PBS containing 0.1% tween-20 after the antibody solution was removed. 50 µl of anti-rabbit antibody conjugated with biotin at 0.1 µg/ml was added into the wells and incubated at room temperature for 30 min. The wells were washed 4 times with PBS containing 0.1% tween-20 after the antibody solution was removed. 50 ul of streptivadin conjugated with HRP was added into the wells and incubated at room temperature for 30 min. After washing 4 times, 100 µl of the color development solution containing TMB was added into the wells and the wells were observed for 2-10 min for a blue color appearance. The 1 M HCl or H₂SO4 solution was added to stop the color development and the optical density was measured with a microplate reader. The results were shown in the FIG. 2.

EXAMPLE 2

The experiment was carried out to determine the sensitivity of the method of this invention for detecting hydroxymethylated DNA.

Figure 3:
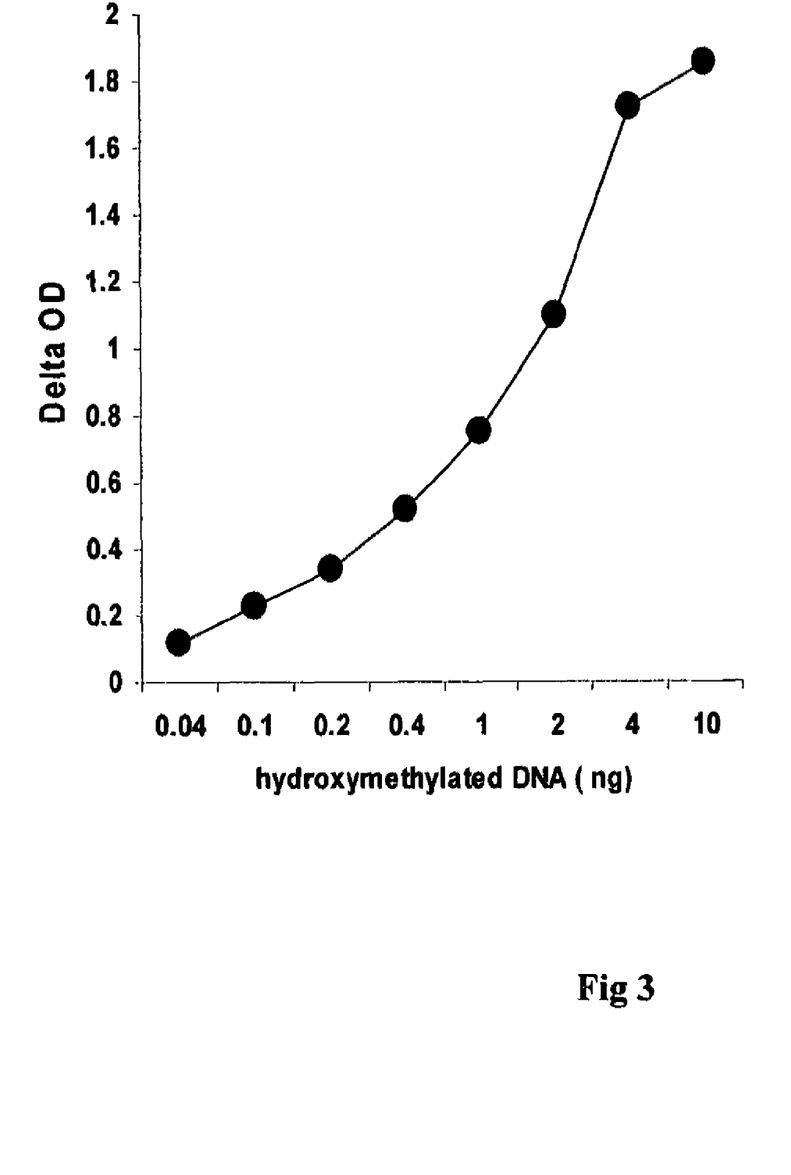
FIG. 3 shows the sensitivity of the method of this invention in detecting hydroxymethylated DNA. The experiment was carried out as described in Example 2.

100 μl of the DNA high-binding solution based on this invention are added into polystyrene 8-well strips followed by adding 5 μl of hydroxymethylated MLH1 amplicon at different concentrations. The strips were then incubated at 37° C. for 1.5 h followed by washing 3 times. 50 μl of polyclonal anti-5-hmC antibody was then added at 0.5 μg/ml and incubated at room temperature for 1 h. The wells were washed 3 times with PBS containing 0.1% tween-20 after the antibody solution was removed. 50 μl of anti-rabbit antibody conjugated with biotin at 0.1 μg/ml was added into the wells and incubated at room temperature for 30 min. The wells were washed 4 times with PBS containing 0.1% tween-20 after the antibody solution was removed. 50 ul of streptivadin conjugated with HRP was added into the wells and incubated at room temperature for 30 min. After washing 4 times, 100 μl of the color development solution containing TMB was added into the wells and the wells were observed for 2-10 min for a blue color appearance. The 1 M HCl or H₂SO4 solution was added to stop the color development and the optical density was measured with a microplate reader. As shown in FIG. 3, as low as 40 pg of hydroxymethylated DNA was detected.

EXAMPLE 3

The experiment was carried out to examine the specificity of the method based on this invention in detecting hydroxymethylated DNA.

Figure 4:
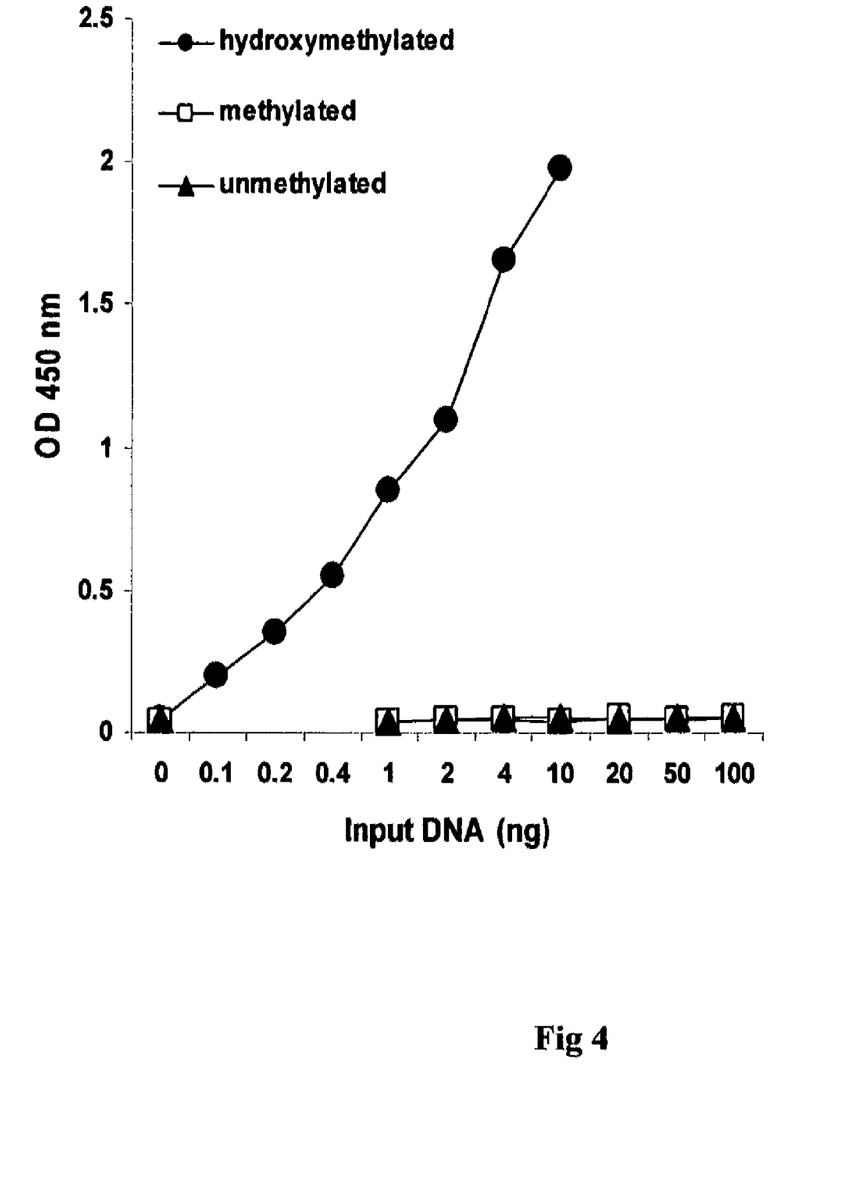
FIG. 4 shows the specificity of the method of this invention in detecting hydroxymethylated DNA. The experiment was carried out as described in Example 3.

100 μl of the DNA high-binding solution based on this invention are added into polystyrene 8-well strips. 5 ul of hydroxymethylated MLH1 amplicons, methylated MLH1 amplicons, and unmethylated MLH1 amplicons at different concentrations were then added into the wells, respectively. The strips were then incubated at 37° C. for 1.5 h followed by washing 3 times. 50 μl of polyclonal anti-5-hmC antibody was then added at 0.5 μg/ml and incubated at room temperature for 1 h. The wells were washed 3 times with PBS containing 0.1% tween-20 after the antibody solution was removed. 50 μl of anti-rabbit antibody conjugated with biotin at 0.1 μg/ml was added into the wells and incubated at room temperature for 30 min. The wells were washed 4 times with PBS containing 0.1% tween-20 after the antibody solution was removed. 50 μl of streptivadin conjugated with HRP was added into the wells and incubated at room temperature for 30 min. After washing 4 times, 100 μl of the color development solution containing TMB was added into the wells and the wells were observed for 2-10 min for a blue color appearance. The 1 M HCl or H₂SO4 solution was added to stop the color development and the optical density was measured with a microplate reader. As shown in FIG. 4, only hydroxymethylated DNA is detected with the method of this invention.

EXAMPLE 4

The experiment was carried out to examine the ability for quantifying hydroxymethylated DNA in normal and cancer cells.

Figure 5:
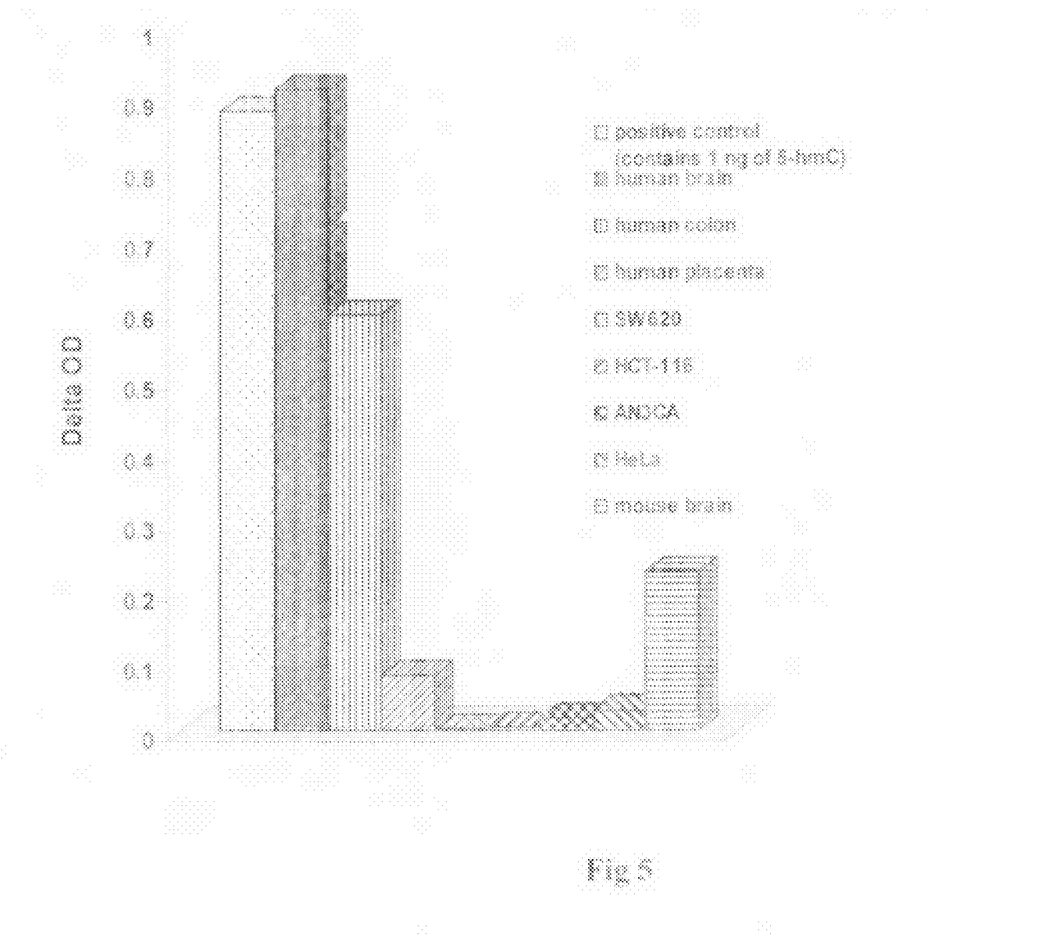
FIG. 5 shows the quantification of hydroxymethylated DNA in normal and cancer cells. The experiment was carried out as described in Example 4. The positive control contains 1 ng of 5-hmC.

100 μl of the DNA high-binding solution based on this invention are added into polystyrene 8-well strips. 5 μl (200 ng) of various genomic DNA were then added into the strip wells. The DNA is isolated from normal human brain, human placenta, human colon, colon cancer cell lines HT116 and SW620, endometrial cancer cell line AN3CA, cervical cancer cell line Hela, and mouse brain respectively. The strips were then incubated at 37° C. for 1.5 h followed by washing 3 times. 50 μl of polyclonal anti-5-hmC antibody was then added at 0.5 μg/ml and incubated at room temperature for 1 h. The wells were washed 3 times with PBS containing 0.1% tween-20 after the antibody solution was removed. 50 μl of anti-rabbit antibody conjugated with biotin at 0.1 μg/ml was added into the wells and incubated at room temperature for 30 min. The wells were washed 4 times with PBS containing 0.1% tween-20 after the antibody solution was removed. 50 ul of streptivadin conjugated with HRP was added into the wells and incubated at room temperature for 30 min. After washing 4 times, 100 μl of the color development solution containing TMB was added into the wells and the wells were observed for 2-10 min for a blue color appearance. The 1 M HCl or H₂SO4 solution was added to stop the color development and the optical density was measured with a microplate reader. The results are shown in FIG. 5 and table 1.

TABLE 1

% Content of 5-hmC in normal and cancer cells

| Cells | Input DNA(ng) | 5-hmC (ng) | % Content of 5-hmC |
|---|---|---|---|
| Human brain | 200 | 1.18 | 0.69 |
| Human colon | 200 | 0.92 | 0.46 |
| Placenta | 200 | 0.12 | 0.06 |
| HCT-116 | 200 | 0.006 | 0.003 |
| SW620 | 200 | 0.006 | 0.003 |
| AN3CA | 200 | 0.024 | 0.012 |
| HeLa | 200 | 0.04 | 0.02 |
| Mouse brain | 200 | 0.28 | 0.14 |

What is claimed is:

1. A method of rapidly quantifying hydroxymethylated DNA in a DNA sample comprising:
   a) the binding of the DNA sample to a plastic carrier at an appropriate temperature for an appropriate time period with a DNA binding solution containing at least three salt reagent selected from sodium and ammonium salts or contains multiple sodium and ammonium salts at an appropriate concentration and in an appropriate ratio of each salt; wherein the appropriate temperature is from 25° C. to 37° C., the sodium salt is sodium chloride in an amount of 0.3 M to 3M, or sodium sulfate in an amount of 0.5 M to 3M, and the ammonium salt is ammonium chloride in an amount of 0.06 M to 3M or ammonium sulfate in an amount of 0.3 M to 3M,
   wherein the appropriate ratio is sodium chloride to ammonium sulfate to ammonium chloride at 5:5:1 in said binding solution;
   b) the addition of an anti-5-hydroxymethylcytosine structure antibody that reacts with 5-hydroxymethylcytosine contained in the DNA to form immuno-reaction products; c) the determination of said immuno-reaction products with a signal reporter; and d) the quantification of hydroxymethylcytosine amount in said DNA sample by comparing signal intensity generated from said DNA sample with that from hydroxymethylated DNA standard control.

2. The method according to claim 1 wherein said DNA samples are from tissues or cells of mammalian, or eukaryotic, or plant origin.

3. The method according to claim 1 wherein said plastic carrier is a polystyrene multi-well plate.

4. The method according to claim 1 wherein said plastic carrier is a polystyrene multi-well strip.

5. The method according to claim 1 wherein said plastic carrier is a polystyrene microscope slide.

6. The method according to claim 1 wherein said plastic carrier is polystyrene beads.

7. The method according to claim 1 wherein said appropriate period is from 0.5 to 3 hours.

8. The method according to claim 1 wherein said 5-hydroxymethylcytosine structure is 5-hydroxymethylcytosine.

9. The method according to claim 1 wherein said 5-hydroxymethylcytosine structure is 5-hydroxymethylcytidine.

10. The method according to claim 1 wherein said 5-hydroxymethylcytosine structure is 5-hydroxymethyl-2'-deoxycytidine.

11. The method according to claim 1 wherein said anti-5-hydroxymethylcytosine structure antibody is selected from mouse monoclonal anti-5-hydroxymethylcytosine, mouse monoclonal anti-5-hydroxymethylcytidine, rat monoclonal anti-5-hydroxymethylcytosine, rabbit polyclonal anti-5-hydroxymethylcytidine, goat polyclonal anti-5-hydroxymethylcytosine, and sheep polyclonal anti-5-hydroxymethylcytidine, preferably mouse monoclonal anti-5-methylcytosine and rabbit polyclonal anti-5-methylcytidine.

12. The method according to claim 1 wherein said signal reporter is selected from peroxidase-streptavidin, anti-rabbit antibody conjugated with horse radish peroxidase (HRP), alkaline phosphotase (AP), biotin, or fluorescent dye.

* * * * *